United States Patent
Stopher et al.

(10) Patent No.: US 6,685,613 B1
(45) Date of Patent: Feb. 3, 2004

(54) METHOD OF MAKING A PREFASTENED UNDERGARMENT IN A CROSS MACHINE DIRECTION AND APPARATUS FOR CARRYING OUT SAID METHOD

(75) Inventors: James Bennington Stopher, Neenah, WI (US); Robert Eugene Vogt, Neenah, WI (US); Timothy J. Blenke, Neenah, WI (US); Patrick S. McNichols, Hortonville, WI (US); Robert Micheal Letterman, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 214 days.

(21) Appl. No.: 09/604,607

(22) Filed: Jun. 27, 2000

(51) Int. Cl.⁷ ................................. B31B 49/04
(52) U.S. Cl. ................. 493/194; 493/254; 493/422; 493/208
(58) Field of Search ................ 493/194, 208, 493/254, 422; 156/73.1, 200, 204

(56) References Cited

U.S. PATENT DOCUMENTS

| | | | |
|---|---|---|---|
| 2,798,489 A | * | 7/1957 | Behrman |
| 3,653,381 A | * | 4/1972 | Warnken |
| 3,994,486 A | | 11/1976 | Nystrand |
| 4,409,052 A | * | 10/1983 | Agris et al. |
| 4,650,530 A | | 3/1987 | Mahoney et al. |
| 5,080,741 A | | 1/1992 | Nomura et al. |
| 5,690,627 A | * | 11/1997 | Clear et al. |
| 5,779,831 A | | 7/1998 | Schmitz |
| 5,855,574 A | * | 1/1999 | Kling et al. .......... 156/204 |
| 5,879,500 A | | 3/1999 | Herrin et al. |
| 5,897,545 A | * | 4/1999 | Kline et al. |
| 6,022,432 A | | 2/2000 | Elsberg et al. |

FOREIGN PATENT DOCUMENTS

| | | |
|---|---|---|
| FR | 2219636 | 9/1974 |
| WO | WO 96/20076 | 7/1996 |

* cited by examiner

*Primary Examiner*—Eugene Kim
*Assistant Examiner*—Sameh Tawfik
(74) *Attorney, Agent, or Firm*—Pauley Petersen & Erickson

(57) ABSTRACT

A method of making a prefastened refastenable diaper or other undergarment includes the steps of forming a web of diaper material, cutting holes in the center of the web as precursor leg cutouts and, placing a fastening system divided between front and back waist sections onto each diaper section of the web to prepare inchoate diapers having their long axes in the cross machine direction of the web. Then the web is cut to define the web into individual diapers. The diapers are then folded in half at the crotch section, placing the fastening system section in lapping alignment and fastening the system together. The diapers are then removed by the leg holes to bundle and place the diapers in point of sale containers. The method lends itself to simple in-line process machinery for accomplishing the manufacture of the diapers. The method creates diapers which are useful upon removal from the point of sale container as pull on training pants and which may be easily removed in the fashion of a diaper by separating the fasteners.

13 Claims, 6 Drawing Sheets

METHOD OF MAKING A PREFASTENED UNDERGARMENT IN A CROSS MACHINE DIRECTION AND APPARATUS FOR CARRYING OUT SAID METHOD

BACKGROUND OF THE INVENTION

1. Field of the Invention

The present invention relates generally to means for making diapers, or other undergarments, especially as related to incontinence products. The present invention relates specifically to a diaper which is prefastened in its point of sale container so that the diaper may be used as a pull on type training pant but may be removed like a regular diaper by separating the front and rear waist portions thru disengaging the refastenable fastening means holding the front and rear together. The present invention relates even more specifically to a method of making such prefastened diapers when the diapers are laid out as in-process or precursor diapers, on a web, with their long axes in the cross machine, or cross, direction of the web.

2. Discussion of the Related Art

There are two basic ways of manufacturing diapers from a web. One is to place the long axis of the diapers in the machine direction, also referred to as longitudinal or X-axis, of the web, with leg cutouts on the edges of the web. The second is to place the long axis of the diaper in the cross machine direction or Y-axis of the web with leg cutouts being formed from holes placed centrally in the web. These methods are generally illustrated in FIGS. 1 and 2, respectively.

In the known art, there have been two ways of making the diaper web into point of sale items. One is to put refastenable tabs, such as adhesive tape or hook and loop combinations onto the diaper body, in the manner of an infant diaper, for later use to secure the back panel of the diaper to the front panel. A second is to bond the side edges of the front and back waist sections together to make a fixed waist band, in the manner of a training pant which is slid on and off the wearer like a regular adult garment. To remove such a garment if it becomes soiled it is necessary to break the waist band bond in order to remove the garment like a diaper, as convenience and hygiene would dictate. A simple flange seam where two inside surfaces are abutted and bonded is known in the art for the above mentioned waist seam. For example see FIG. 5 of Mahoney et al., U.S. Pat. No. 4,650,530. Lap seams, wherein the surfaces to be joined are overlapped, outside surface to inside surface, are also known for diapers made in the machine direction or turned mechanically to be as if made in the machine direction, as taught in PCT International Application No. WO 96/20076 to Schmitz/The Procter & Gamble Company. While Schmitz teaches a method of accurate folding and placement of the overlapping areas of joining when presented preforms in the machine direction, the machinery involved in the process is quite complicated mechanically.

It is therefore desired to provide a training pant which may be slid-on in the fashion of an adult garment while being easily removeable in the manner of a diaper and which is made with relatively uncomplicated machinery.

SUMMARY OF THE INVENTION

In order to provide the desired object the present invention provides a point of sale diaper garment which is prefastened using refastenable fasteners as its sole closing means for front-to-back panel closure.

The present invention further provides means for accomplishing an accurate prefastening of a refastenable garment which is made in the cross machine direction. The present invention further provides a simple means for the making and packaging of the prefastened refastenable garment leading to overall gains in production speed.

The present invention provides method and means for making diapers in the cross machine direction on a web, separating individual diapers from the web, using a rotary wheel for folding the diapers in half, properly aligning the refastenable fasteners and pre-fastening them, then removing the prefastened diapers for packaging, with a mechanically simple and speedy in-line process.

A method of making a prefastened refastenable diaper or other undergarment includes the steps of forming a web of diaper material, cutting holes in the center of the web as precursor leg cutouts/margins, placing elastics, fastening tabs, and other add ones onto the web to prepare inchoate diapers having their long axes in the cross machine direction of the web, cutting the web to separate it into individual diapers, folding the diapers in half at the crotch section, placing the fastening tabs in lapping alignment and fastening the tabs together, then removing the diapers by the leg holes to bundle and place the diapers in point of sale containers. The method lends itself to simple machinery for accomplishing the manufacture of the diapers. The method creates diapers which are useful right out of the point of sale container as pull on training pants and which may be easily removed in the fashion of a diaper by separating the fasteners.

Folding of the diapers for placement on the rotary wheel may be accomplished by belts, cone rollers, vacuum or combinations thereof. Alignment and fastening of the fastening system may also be accomplished mechanically, with vacuum, i.e. negative air pressure; positive air pressure; or combinations thereof. Removal of the pre-fastened diaper for packaging may further be similarly accomplished.

BRIEF DESCRIPTION OF THE DRAWINGS

These and other objects and features of this invention will be better understood from the following detailed description taken in conjunction with the drawings wherein.

DESCRIPTION OF THE PREFERRED EMBODIMENTS

Figure 1:
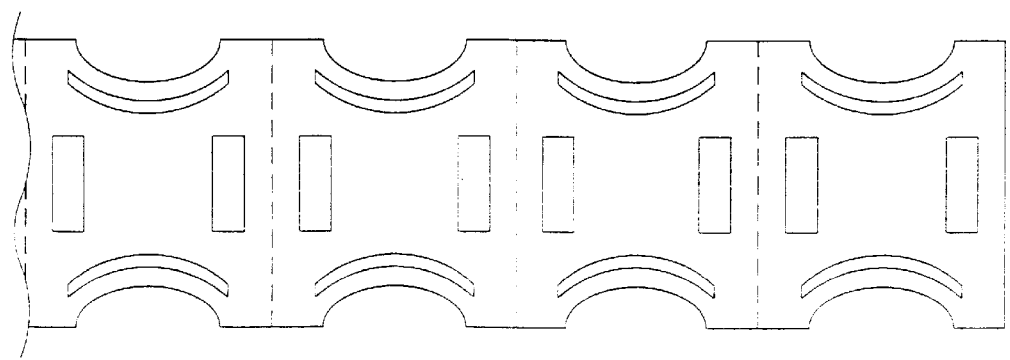
FIG. 1 is a schematic of a known web of precursor diapers manufactured in the machine direction.
Figure 2:
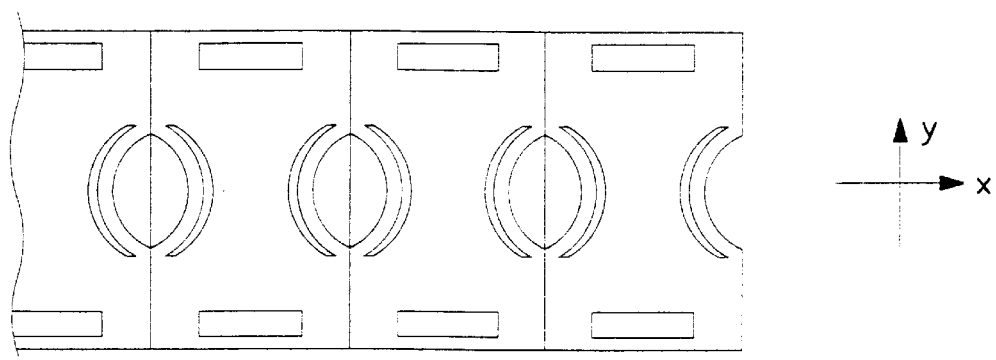
FIG. 2 is schematic of a known web of precursor diapers manufactured in the cross machine direction.
Figure 3:
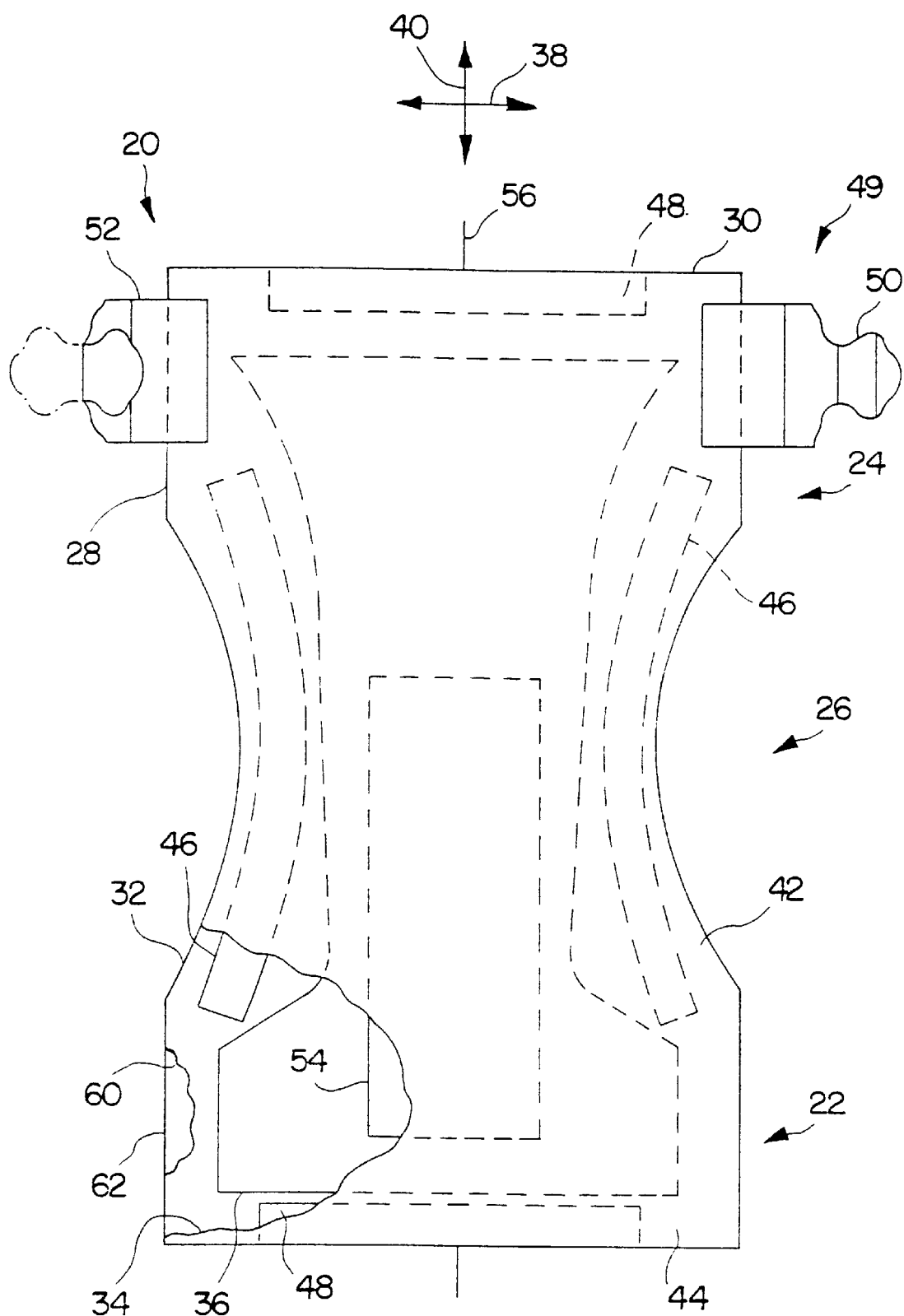
FIG. 3 is a view of a laid open, fully extended, partially cut away top plan view of a known absorbent article, or diaper, useful for teaching the parts thereof as an aid to understanding the present invention.

With reference to FIG. 3, an absorbent garment, such as the disposable diaper 20, generally defines a front waist section 22, a rear waist section 24, an intermediate section 26 which interconnects the front and rear waist sections, a pair of laterally opposed side edges 28, and a pair of longitudinally opposed end edges 30. The front and rear waist sections include the general portions of the article which are constructed to extend substantially over the wearer's front and rear abdominal regions, respectively, during use. The intermediate section of the article includes the general portion of the article which is constructed to extend through the wearer's crotch region between the legs. The opposed side edges 28 define leg openings for the diaper and generally are curvilinear or contoured to more closely fit the legs of the wearer. The opposed end edges 30 define a waist opening for the diaper 20 and typically are straight but may also be curvilinear.

FIG. 3 is a representative plan view of the diaper 20 of the present invention in a flat, uncontracted state. Portions of the structure are partially cut away to more clearly show the interior construction of the diaper 20, and the surface of the diaper which contacts the wearer is facing the viewer. The diaper 20 includes a substantially liquid impermeable, vapor permeable, composite backstreet 32, a porous, liquid permeable topsheet 34 positioned in facing relation with the backsheet 32, and an absorbent body 36, such as an absorbent pad, which is located between the backstreet and the topsheet. The diaper 20 also has a lateral direction 38 and a longitudinal direction 40. Marginal portions of the diaper 20, such as marginal sections of the backsheet 32, may extend past the terminal edges of the absorbent body 36. In the illustrated embodiment, for example, the backsheet 32 extends outwardly beyond the terminal marginal edges of the absorbent body 36 to form side margins 42 and end margins 44 of the diaper 20. The topsheet 34 is generally coextensive with the backsheet 32 but may optionally cover an area which is larger or smaller than the area of the backsheet 32, as desired.

To provide improved fit and to help reduce leakage of body exudates from the diaper 20, the side margins 42 and end margins 44 of the diaper may be elasticized with suitable elastic members, such as leg elastic members 46 and waist elastic members 48. For example, the leg elastic members 46 may include single or multiple strands of elastic or elastomeric composites which are constructed to operably gather and shirr the side margins 42 of the diaper 20 to provide elasticized leg bands which can closely fit around the legs of the wearer to reduce leakage and provide improved comfort and appearance. Similarly, the waist elastic members 48 can be employed to elasticize the end margins 44 of the diaper 20 to provide elasticized waistbands. The waist elastics are configured to operably gather and shirr the waistband sections to provide a resilient, comfortably close fit around the waist of the wearer.

The diaper 20, as representatively illustrated in FIG. 3, may further include a fastening system 49 illustrated by a pair of fasteners 50 which are employed to secure the diaper 20 about the waist of a wearer. Suitable fasteners 50 include hook-and-loop type fasteners, adhesive tape fasteners, buttons, pins, snaps, mushroom-and-loop fasteners, and the like. A cooperating side panel member 52 can be associated with each fastener and may be constructed to be nonelasticized, or to be elastically stretchable at least along the lateral direction 38 of the diaper 20. In the case of training pants, additional web material may be added to the fastening system 49 and arranged under the fasteners 50 to be lightly bonded to the front waist section 22 to provide a more pant-like feel and yet be easily broken away to permit removal like a diaper.

The various components of the diaper 20 are assembled together employing various types of suitable attachment means, such as adhesive, sonic bonds, thermal bonds or combinations thereof.

Figure 4:
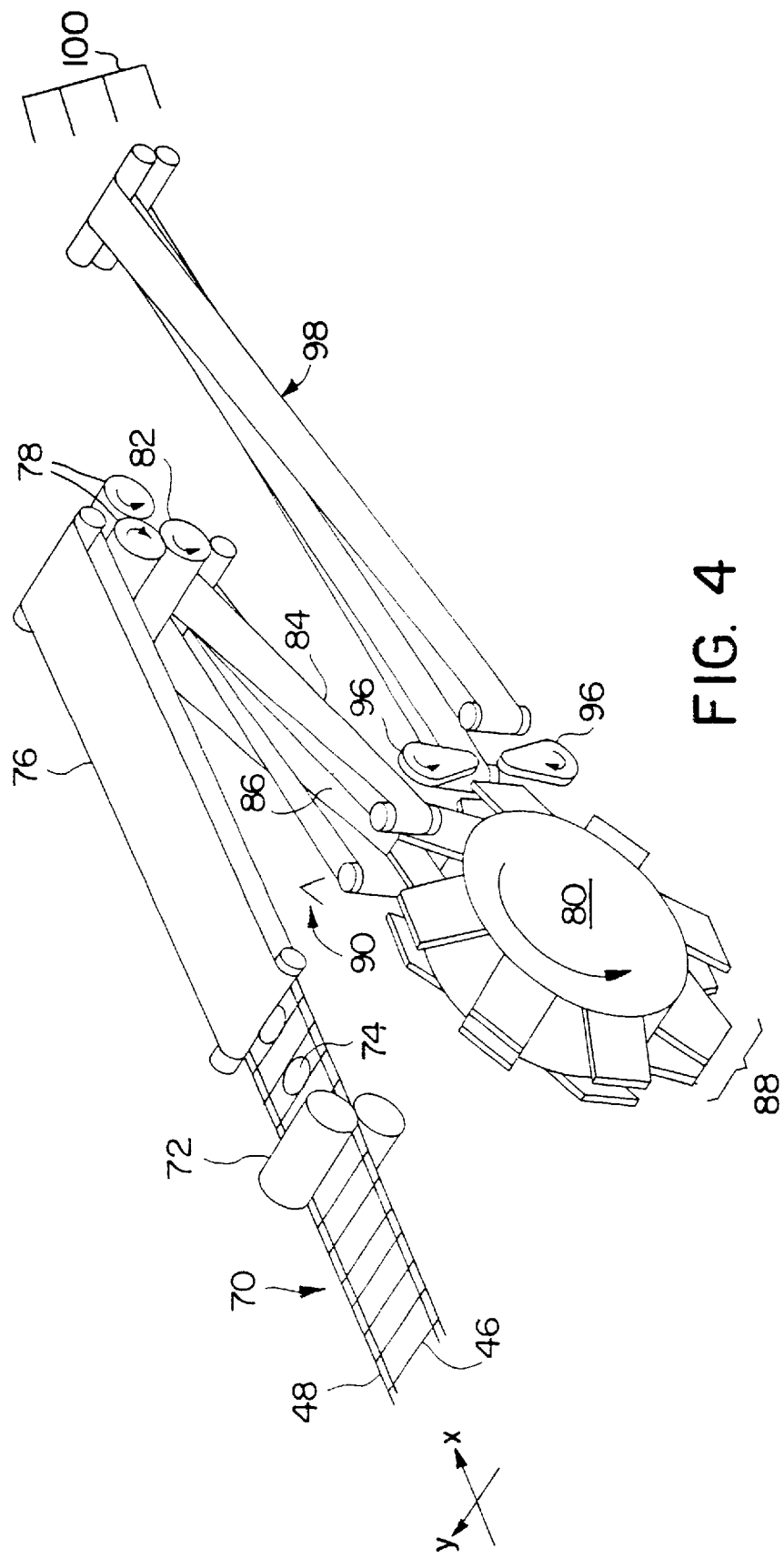
FIG. 4 shows a first embodiment of the present invention.

Referencing FIG. 4, a web 70 of precursor diapers is shown traveling in the machine, or X-axis direction with waist elastics 48 and leg elastics 46 in place indicating the long axis of the diaper in the cross direction or Y-axis. A first rolling die cutter 72 cuts leg holes 74 in the central portion of the web. The web 70 is then transferred to a vacuum conveyor 76 to maintain the web in a tensioned state, keeping the precursor diapers flat. The web 70 is then sectioned by a second rolling die cutter 78 into individual diapers (not shown for clarity of illustration). While shown as die cutters, the leg cutting and diaper separating means are not intended to be limited to one type of cutting means. Also, e.g. the second die cutter 78 may be constructed and arranged to perform a perforation cut rather than a through cut leaving the diapers defined individually but needing to be separated by tensioning forces on the rotary wheel 80, as further explained below.

The individual diapers (or perforated web) are fed through a counter roller 82 and picked up by a horizontal-to-vertical twisted belt 84 running on either side of an inclined folding projection 86 leading to the rotary wheel 80. The diaper is folded in an inverted "V" shape with its crotch area up and with waist bands down by the time the diaper reaches the rotary wheel 80 to be accepted by open, inverted "V"-shaped protrusions 88 on the wheel. An inverted "V" 90 in the drawing indicates the diaper orientation on the inclined folding projection 86.

Figure 6:
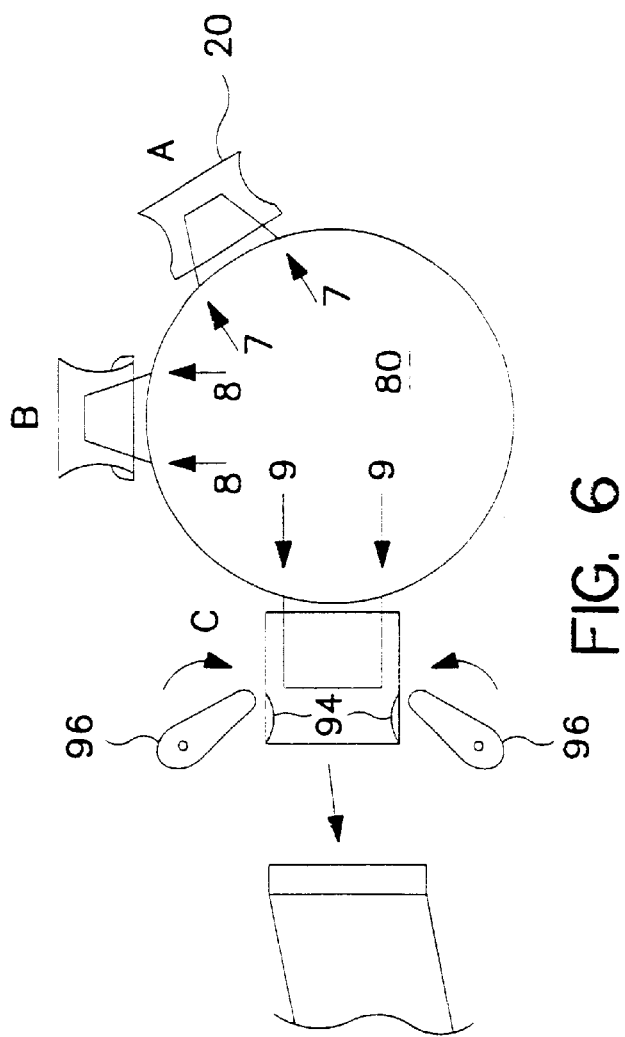
FIG. 6 shows a highly schematic side view of the rotary wheel of FIG. 5 with folded diapers thereon.
Figure 9:
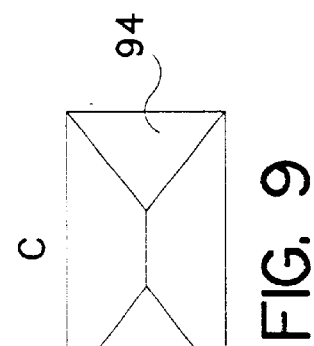
FIG. 9 is a view of a diaper taken along lines 9—9 of FIG. 6.
Figure 8:
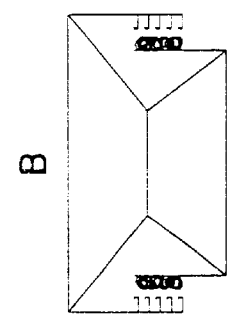
FIG. 8 is a view of a diaper taken along lines 8—8 of FIG. 6.
Figure 7:
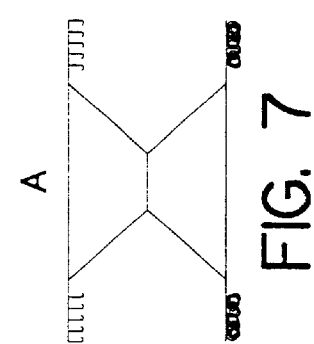
FIG. 7 is a view of a diaper taken along lines 7—7 of FIG. 6.

The diaper may be held in place on the protrusions 88 by vacuum or other suitable means. While the rotary wheel 80 is turning with the diaper 20, as shown in FIG. 6, the diaper 20 is accepted onto the wheel as at position A in the originally folded state (see FIG. 7 also). The fasteners are aligned as at Position B (see FIG. 8 also) and closed or fastened together at position C (see FIG. 9 also). Mechanical armatures, fingers with cam action, etc., such as modified versions of the apparatus set forth in U.S. Pat. No. 4,650,530 to Mahoney et al., which is incorporated herein to the extent necessary for understanding the present invention, may suitably accomplish the folding and may be assisted by controlled vacuum slots or the like within the protrusions 88. In such instance, the protrusions may be completely walled in instead of being the open paddle design illustrated. Arrangement of the exact mechanical structure and/or vacuum slots for folding etc. will be dependent upon several factors and is left to the artisan of ordinary skill in accordance with the teachings of the present invention. The prefastened diaper at Position C presents its leg holes collectively 94, to a pair of orbital pickers, collectively 96, which engage the leg holes 94 and remove the fastened diaper from rotary wheel 80 and place it in a vertical-to-horizontal twisted removal belt 98 which carries the diaper to a known stacking apparatus 100 to facilitate packaging of the folded and fastened diapers in point of sale containers. It will be appreciated that where the fastening system 50 of diaper 20 extends undesirably beyond the basic rectangular shape of the folded diaper when fastened, the extended portions of the pre-fastened fastening system may also be tucked into the body of the diaper at the exit of the removal belt 98 according to known apparatus to present a clean rectangular form to the stacker 100.

Figure 5:
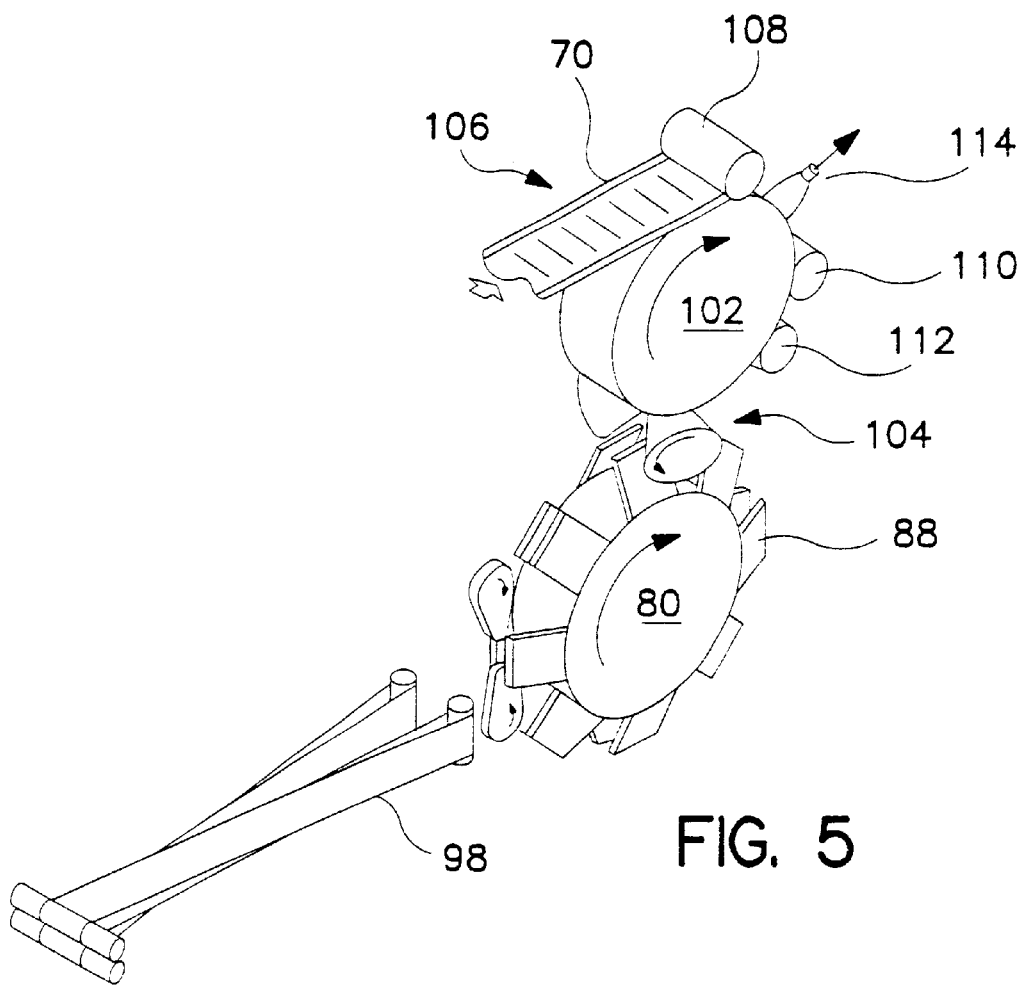
FIG. 5 shows a second embodiment of the present invention.
Figure 10:
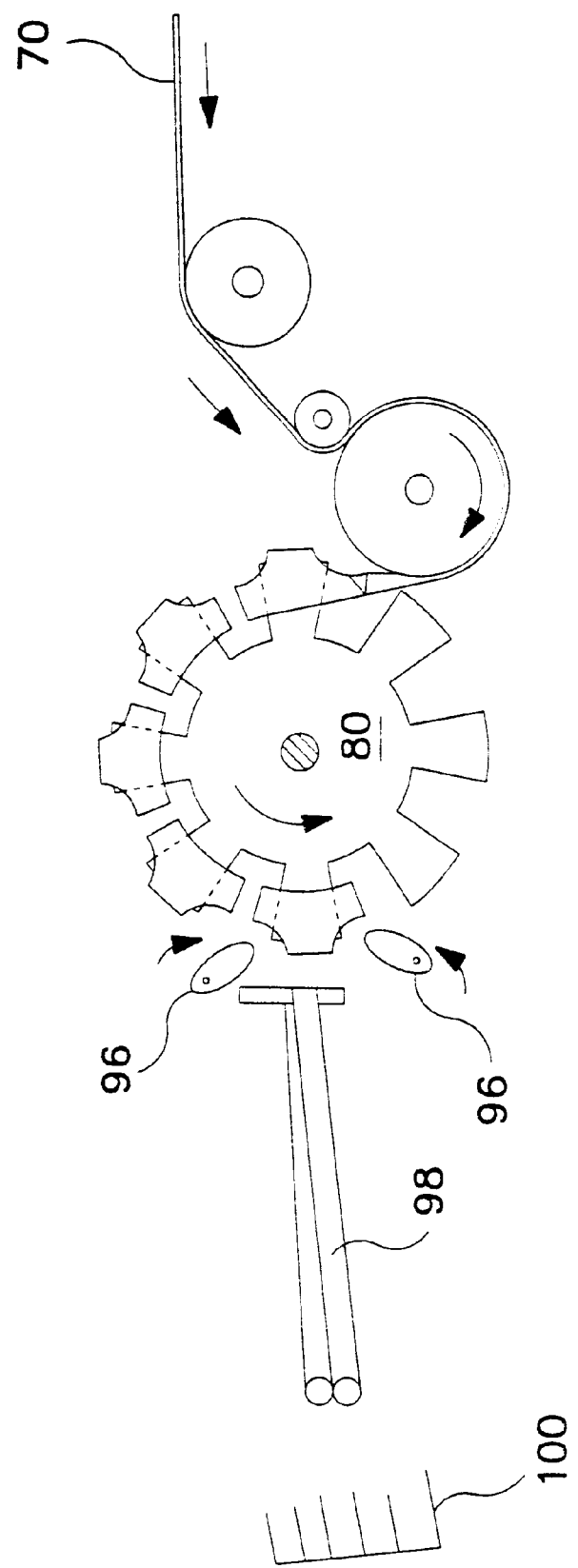
FIG. 10 shows a third embodiment of the present invention.

Referencing FIG. 5, an alternative arrangement of the apparatus of FIG. 4 is shown. The horizontal-to-vertical belt 84 and the inclined folding projection 86 of FIG. 4 have been replaced by a rotating drum 102 and a rotating dual cone folding process 104 which transfer the diaper between the linear web travel 106 and onto the rotary wheel 80 with its protrusions 88. Vacuum beneath the surface of the rotating drum 102 maybe used to hold the web of precursor diapers in place. Multiple die cutters may be variously placed on the drum 102 as a leg cut out cutter 108, and front panel and back panel cutters 110, 112, respectively. A trim removal vacuum 114 is also shown downstream of the leg cut out cutter 108. Referencing FIG. 10, as another alternative, where a perforate cut is used instead of severing the web completely, the web may be fed directly to the rotary wheel 80 in the manner of Mahoney et al. and the diapers will be individuated while upon the wheel 80 through either inherent or added strain on the web 70. The diapers are then removed by the orbital pickers 96 into the vertical-to-horizontal belt 98 and the stacker 100.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A method for creating a lap seam on a diaper whose long axis lies in the cross machine direction of a web, comprising:
   a) running a web of diaper material in a machine direction;
   b) cutting holes in a central portion of said web;
   c) cutting the web in a cross machine direction to define individual diapers;
   d) folding said individual diapers to a folded position at an intermediate section of the diapers along a medial line of a longitudinal axis of the web;
   e) mounting a folded diaper onto a rotary wheel having protrusions thereon for receiving folded diapers, the folded diaper being on one protrusion and having a front waist section on a first surface of a protrusion and a rear waist section being on a second surface of the protrusion and in said folded position with the front and rear waist sections being proximal to a center of said wheel and the intermediate section of the diaper being distal from the center of said wheel, each of the front and rear waist sections having left and right lateral side margins;
   f) detaching the left and right lateral side margins of each of the front and rear waist sections from the web;
   g) folding the detached side margins of the front and rear waist sections of each lateral side of the folded diaper together in lapping relationship and fastening the front and rear waist sections together thereby creating a fastened diaper with leg holes and lapped side seams; and
   h) picking the fastened diaper with lapped side seams off the protrusion.

2. The method for creating a lap seam on a diaper according to claim 1, further including the step of: picking the fastened diaper off the protrusion by engaging the leg holes of the diaper with rotating lobes.

3. The method for creating a lap seam on a diaper according to claim 1, further including the step of: folding the side margins by one of a method selected from the group comprising: application of vacuum, manipulation by mechanical fingers, and combination of vacuum and mechanical fingers methods.

4. The method for creating a lap seam on a diaper according to claim 1, further including the step of: tucking the fastened waist sections into a body cavity of the diaper.

5. The method for creating a lap seam on a diaper according to claim 1, further including the step of: tacking fasteners and cooperating side panel members onto the diaper web to serve as a fastening system.

6. The method for creating a lap seam on a diaper according to claim 1, wherein the front and rear waist sections include refastenable fasteners.

7. The method for creating a lap seam on a diaper according to claim 1, wherein the diaper includes a fastening system attached to a rear waist section of each lateral side of the diaper.

8. The method for creating a lap seam on a diaper according to claim 1, wherein the fastening step includes applying an adhesive between front and rear waist sections of the diaper.

9. The method for creating a lap seam on a diaper according to claim 1, wherein the step of cutting the web further includes making a perforate line cut without fully separating the web.

10. The method for creating a lap seam on a diaper according to claim 1, wherein the fastening step includes inserting a hook material into a loop material.

11. The method for creating a lap seam on a diaper according to claim 1, wherein the fastening step includes lightly bonding additional web material between front and rear waist sections of each lateral side.

12. A method for creating a lap seam on a diaper whose long axis lies in a cross machine direction of a web, comprising:
   a) running a web of diaper material in a machine direction;
   b) cutting holes in a central portion of said web;
   c) cutting the web in a cross machine direction to define individual diapers;
   d) folding said individual diapers to a folded position at an intermediate section of the diapers along a medial line of a longitudinal axis of the web;
   e) mounting a folded diaper onto a rotary wheel having protrusions thereon for receiving folded diapers, the folded diaper being on one protrusion and having a front waist section on a first surface of a protrusion and a rear waist section being on a second surface of the protrusion and in said folded position with the front and rear waist sections being proximal to a center of said wheel and the intermediate section of the diaper being distal from the center of said wheel;
   f) folding side margins of the front and rear waist sections of each lateral side of the folded diaper together in lapping relationship and fastening the front and rear waist sections together thereby creating a fastened diaper with leg holes; and
   g) picking the fastened diaper off the protrusion; and
   h) picking the fastened diaper off the protrusion by engaging the leg holes of the diaper with rotating lobes.

13. The method for creating a lap seam on a diaper according to claim 12, further including the step of: moving the picked diapers to a position to be placed in a stacking apparatus.

\* \* \* \* \*